(12) United States Patent
Zhao et al.

(10) Patent No.: US 10,695,028 B2
(45) Date of Patent: Jun. 30, 2020

(54) FLOATING MECHANISM AND ULTRASONIC DIAGNOSTIC APPARATUS HAVING SAME

(71) Applicant: SHENZHEN MINDRAY BIO-MEDICAL ELECTRONICS CO., LTD., Shenzhen (CN)

(72) Inventors: Yanqun Zhao, Shenzhen (CN); Rongfu Yang, Shenzhen (CN); Zhiwu Chen, Shenzhen (CN)

(73) Assignee: Shenzhen Mindray Bio-Medical Electronics Co., Ltd., Shenzhen (CN)

( * ) Notice: Subject to any disclaimer, the term of this patent is extended or adjusted under 35 U.S.C. 154(b) by 39 days.

(21) Appl. No.: 15/978,637

(22) Filed: May 14, 2018

(65) Prior Publication Data

US 2018/0344285 A1 Dec. 6, 2018

Related U.S. Application Data

(63) Continuation of application No. PCT/CN2015/094741, filed on Nov. 16, 2015.

(51) Int. Cl.
*F16M 11/00* (2006.01)
*A61B 8/00* (2006.01)
(Continued)

(52) U.S. Cl.
CPC .............. *A61B 8/4405* (2013.01); *A61B 8/44* (2013.01); *A61B 8/462* (2013.01); *F16M 11/043* (2013.01);
(Continued)

(58) Field of Classification Search
CPC ....... F16M 2200/063; F16M 2200/061; F16M 2200/06
(Continued)

(56) References Cited

U.S. PATENT DOCUMENTS

D621,820 S * 8/2010 Liang ........................ D14/239
9,004,430 B2 * 4/2015 Conner ................. F16M 11/08
248/277.1
(Continued)

FOREIGN PATENT DOCUMENTS

CN 101311607 A 11/2008
CN 103629502 A 3/2014
(Continued)

*Primary Examiner* — Steven M Marsh
(74) *Attorney, Agent, or Firm* — Kory D. Chirstensen

(57) ABSTRACT

A floating mechanism comprises a lift arm, a translation arm and a connection frame. One end of the lift arm is rotatably connected to the connection frame which is also rotatably connected to the translation arm. The lift arm drives the translation arm to rotate and move up and down between two intersecting planes with a fulcrum at the other end of the lift arm opposite to the translation arm. The translation arm can also be translated in a translational plane intersecting the lift arm with the connection point of the translation arm and the connecting frame as an axis. The lift arm and the translation arm of the floating mechanism can together drive an operating panel to move up and down in a vertical plane and to translate front and back, and left and right in a translation plane; meanwhile, the operating panel can be driven to rotate in the translation plane along with the lift arm and the translation arm. Also provided are an ultrasonic diagnostic apparatus with the floating mechanism and a floating support method.

22 Claims, 12 Drawing Sheets

(51) Int. Cl.
  *F16M 11/42* (2006.01)
  *F16M 11/08* (2006.01)
  *F16M 11/04* (2006.01)
  *F16M 11/10* (2006.01)
  *F16M 11/20* (2006.01)
  *G01N 29/06* (2006.01)

(52) U.S. Cl.
  CPC ......... *F16M 11/045* (2013.01); *F16M 11/048* (2013.01); *F16M 11/08* (2013.01); *F16M 11/10* (2013.01); *F16M 11/2014* (2013.01); *F16M 11/42* (2013.01); *G01N 29/0609* (2013.01); *F16M 2200/044* (2013.01); *F16M 2200/063* (2013.01)

(58) Field of Classification Search
  USPC ...... 248/276.1, 278.1, 281.11, 919, 920, 921
  See application file for complete search history.

(56) References Cited

U.S. PATENT DOCUMENTS

| | | | |
|---|---|---|---|
| 9,404,618 B2* | 8/2016 | Brown | F16M 11/2014 |
| 2003/0025054 A1* | 2/2003 | Toennesland | A61B 8/00 248/276.1 |
| 2006/0289704 A1 | 12/2006 | Stothers | |
| 2008/0001048 A1* | 1/2008 | Woo | F16M 11/10 248/276.1 |
| 2013/0327911 A1* | 12/2013 | Russell | A47B 17/03 248/276.1 |

FOREIGN PATENT DOCUMENTS

| | | |
|---|---|---|
| CN | 103912777 A | 7/2014 |
| CN | 104869909 A | 8/2015 |
| GB | 2358345 A | 7/2001 |

* cited by examiner

US 10,695,028 B2

FLOATING MECHANISM AND ULTRASONIC DIAGNOSTIC APPARATUS HAVING SAME

TECHNICAL FIELD

The present disclosure relates to mechanical structures, and more particularly to a floating mechanism and an ultrasonic diagnostic apparatus using the same.

BACKGROUND

When medical personnel use medical equipment with a control panel, such as an ultrasonic diagnostic apparatus, it is important that the control panel is able to move flexibly, especially when performing an examination in different postures. The control panel should be cable of a full floating movement, including up-and-down motion, forward-and-backward translation, left-and-right translation, and rotation.

In a traditional control panel, the up-and-down movement and the rotation of the control panel can be achieved primarily in two ways. The first way uses a separate lifting mechanism (in a vertical plane) and a separate forward-and-backward translation and rotation mechanism (in a horizontal plane). In this structure, the up-and-down motion and the forward-and-backward translation and rotation are respectively achieved by two separate mechanisms. The lifting mechanism occupies a large space, and the left-and-right translation of the control panel cannot be achieved. Accordingly, the range of motion of the control panel is limited. The second way uses a separate lifting mechanism (in a vertical plane) and a separate "frog leg" mechanism (in a horizontal plane). The frog leg mechanism is a modified parallel four-bar linkage, of which the fixed end includes tow rotatable pivots which can bring four arms to move. The control panel is fixed at the ends of two arms. This way, the forward-and-backward translation, left-and-right translation and rotation in certain ranges can be achieved. However, in this floating mechanism, the lifting motion and the translation and rotation in a horizontal plane are achieved separately and there is no linkage therebetween.

SUMMARY

Disclosed herein is a floating mechanism and an ultrasonic diagnostic apparatus using the same that can achieve the lifting in a vertical plane and the translation and rotation in a translation plane of the control panel.

In one embodiment, a floating mechanism may be provided. The floating mechanism may include a lifting arm, a rotation arm, and a connection bracket. An end of the lifting arm may be rotatably connected with the connection bracket. The connection bracket may be rotatably connected with an end of the rotation arm. The lifting arm may bring the rotation arm to rotate and lift respectively in two planes intersecting with each other taking the other end of the lifting arm away from the rotation arm as a fulcrum. The rotation arm may rotate in a translation plane intersecting with the lifting arm around a connection point between the rotation arm and the connection bracket.

In one embodiment, a floating mechanism used to connect a first component and a second component may be provided. The floating mechanism may include: a first connection seat which may be connected to the first component through a first revolute pair with a first rotation axis and be able to rotate with respect to the first component around the first rotation axis; a lifting arm which may include a first end and a second end opposite to the first end, where, the first end of the lifting arm may be connected to the first connection seat through a second revolute pair with a second rotation axis and be able to rotate with respect to the first connection seat around the second rotation axis, and the second rotation axis may not be parallel to the first rotation axis; a connection bracket which may be connected to a second end of the lifting arm through a third revolute pair with a third rotation axis and be able to rotate with respect to the lifting arm around the third rotation axis; and a rotation arm which may include a first end and a second end, where, the first end of the rotation arm may be connected to the connection bracket through a fourth revolute pair with a fourth rotation axis and be able to rotate with respect to the connection bracket around the fourth rotation axis, and the fourth rotation axis may not be parallel to the third rotation axis. The second end of the rotation arm may be connected to the second component.

In some embodiments, one end of the lifting arm of the floating mechanism may be rotatably connected with the rotation arm through the connection bracket such that the rotation arm can be rotated in a plane intersecting with the lifting arm taking the connection point between the rotation arm and the connection bracket as the axis. In addition, the lifting arm can also bring the rotation arm to rotate and lift in two planes intersecting with each other taking the end of the lifting arm away from the rotation arm as a fulcrum. This way, the lifting arm and the rotation arm can collectively bring the control panel to lift and rotate in two intersecting planes and translate forward or backward or to the left or to the right in a translation plane. The floating mechanism has large operation range, good linkage and small occupied space, and can achieve the lifting, translation, and rotation simultaneously.

DETAILED DESCRIPTION

In order to facilitate an understanding to the present disclosure, a more detailed description will be provided below with reference to the drawings in which some embodiments are shown. However, the present disclosure can also be implemented in many other ways and is not limited to the embodiments described below.

In the present disclosure, when a component is "fixed" to another component, it may be directly fixed to the other component, or there may also be one or more intermediate components. When a component is "connected" to another component, is may be directly connected to said another component, or there may also be one or more intermediate components.

Unless otherwise defined, all technical and scientific terms used in the present disclosure may have the same meaning to the usual understanding by a person skilled in the art to which the present disclosure belongs. The term "and/or" may include any and all combinations of one or more listed items.

Figure 1:
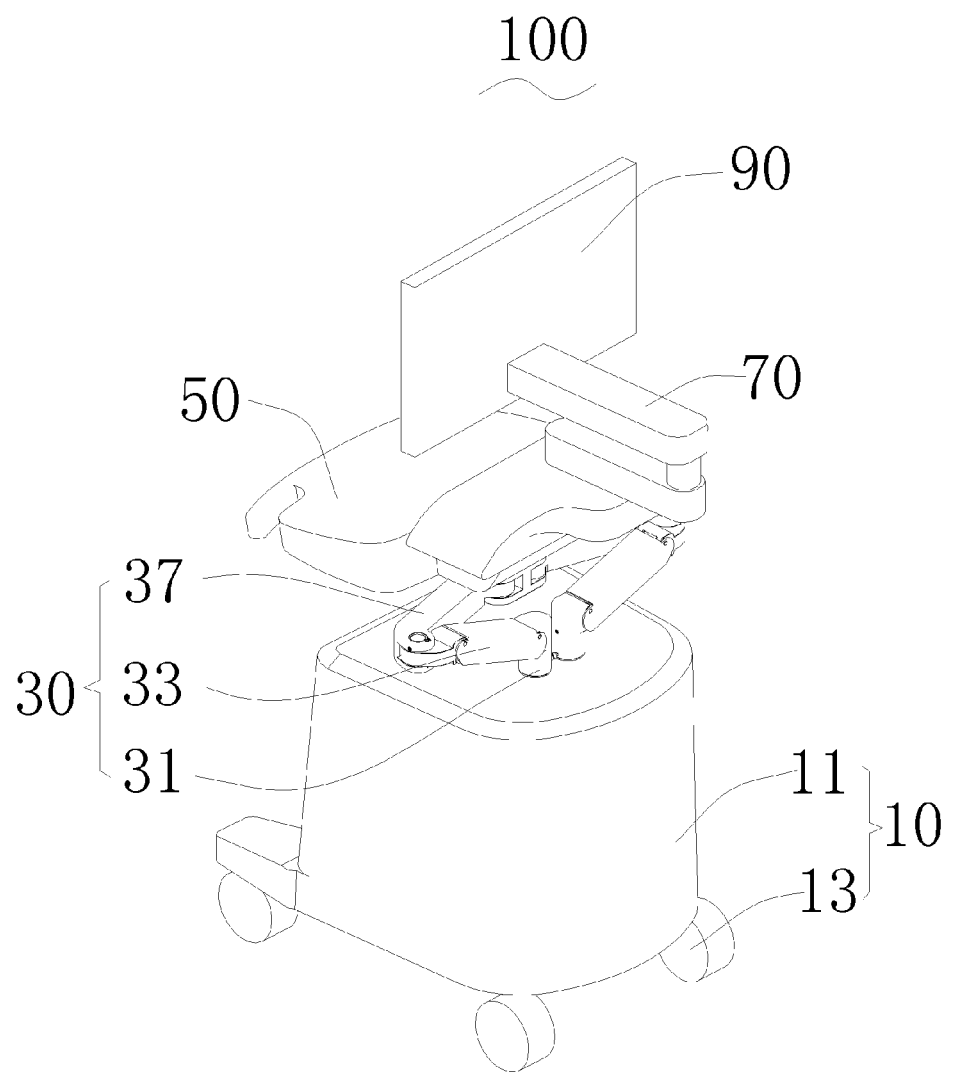
FIG. 1 schematically shows an ultrasonic diagnostic apparatus having a floating mechanism of one embodiment.

FIG. 1 schematically shows an ultrasonic diagnosis apparatus 100 of one embodiment. For convenience of description, only components related to the embodiment of the present disclosure are shown. The ultrasonic diagnosis apparatus 100 may include a main body 10, a floating mechanism 30, a control panel 50, a support arm 70 and a display 90.

The main body 10 may include a frame 11 and several wheels 13. The wheels 13 may be arranged at the bottom of the frame 11 to enable the ultrasonic diagnosis apparatus 100 to move.

In some embodiments, the floating mechanism may connect two components (which are generally referred to as a "first" component and a "second" component). For example, in one embodiment, the floating mechanism may connect the frame 11 and the control panel 50 (e.g., the embodiment in FIG. 1). In this embodiment, the first component may be the frame 11 or the control panel 50, and the second component may correspondingly be the control panel 50 or the frame 11. In one embodiment, the floating mechanism may connect the control panel 50 and the display 90 (e.g., the embodiment in FIG. 2). In this embodiment, the first component may be the control panel 50 or the display 90, and the second component may correspondingly be the display 90 or the control panel 50. In one embodiment, the floating mechanism may directly connect the frame 11 and the display 90 (not shown in the figures). In this embodiment, the first component may be the frame 11 or the display 90, and the second component may correspondingly be the display 90 or the frame 11.

It should be understood that, in other embodiments, the floating mechanism may also be used in other situations in which this kind of floating mechanism is needed to connect components.

Figure 3:
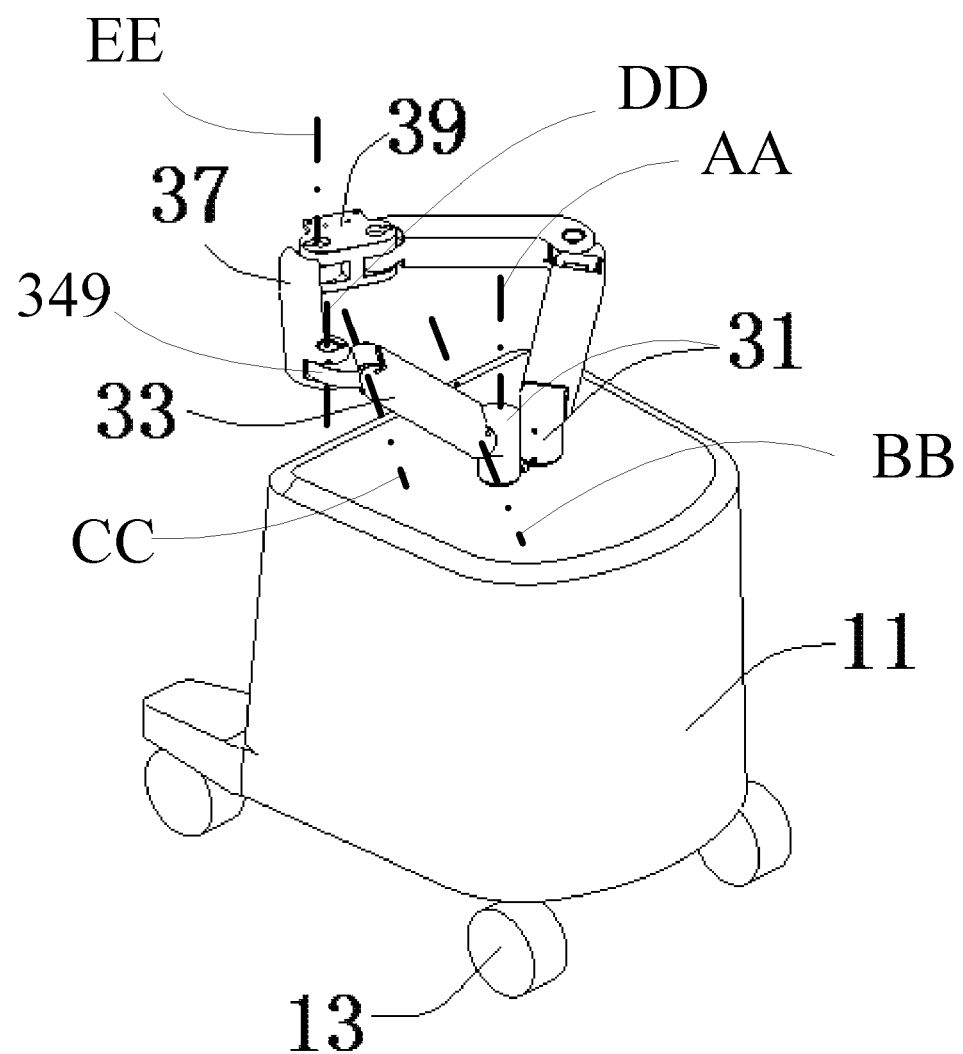
FIG. 3 shows parts of the ultrasonic diagnostic apparatus of FIG. 1.

Referring to FIG. 3, in one embodiment, the floating mechanism 30 may include a first connection seat 31, a lifting arm 33, a connection bracket 349 and a rotation arm 37.

The first connection seat 31 may be connected to the first component of the two components connected by the floating mechanism 30. For example, as shown in FIG. 3, the first connection seat 31 may be connected to the first component through a first revolute pair with a first rotation axis AA, and be able to rotate with respect to the first component by the first revolute pair around the first rotation axis AA.

The lifting arm 33 may include a first end and a second end opposite to the first end. The first end of the lifting arm 33 may be connected to the first connection seat 31 through a second revolute pair with a second rotation axis BB and be able to rotate with respect to the first connection seat 31 by the second revolute pair around the second rotation axis BB. The second rotation axis BB may not be parallel to the first rotation axis AA.

The connection bracket 349 may be connected to the second end of the lifting arm 33 through a third revolute pair with a third rotation axis CC, and be able to rotate with respect to the lifting arm 33 by the third revolute pair around the third rotation axis CC.

The rotation arm 37 may include a first end and a second end opposite to the first end. The first end of the rotation arm 37 may be connected to the connection bracket 349 through a fourth revolute pair with a fourth rotation axis DD, and be able to rotate with respect to the connection bracket 349 by the fourth revolute pair around the fourth rotation axis DD. The fourth rotation axis DD may not be parallel to the third rotation axis CC.

The second end of the rotation arm 37 may be connected the second component of the two components connected by the floating mechanism 30.

This way, the first component may be connected to the second component through the floating mechanism.

In some embodiments, the first rotation axis AA of the first revolute pair may not be parallel to the second rotation axis BB of the second revolute pair, and the first rotation axis AA may be located in the same or different planes with the second rotation axis BB. For example, in one embodiment, the first rotation axis AA may intersect with the second rotation axis BB. In this case, the first rotation axis AA may or may not be perpendicular to the second rotation axis BB.

In the present disclosure, one rotation axis being "perpendicular" to the other rotation axis may be that, in the case that the two rotation axes are located in the same plane, they are perpendicular to each other, and in the case that the two rotation axes are not located in the same plane, they are spatially perpendicular to each other, i.e. the projection of one rotation axis on the plane in which the other rotation axis is located is perpendicular to said other rotation axis.

In the present disclosure, one rotation axis "intersecting" with the other rotation axis may be that, in the case that the two rotation axes are located in the same plane, they intersect with each other, and in the case that the two rotation axes are not located in the same plane, the projection of one rotation axis on the plane in which the other rotation axis is located intersects with said other rotation axis.

In one embodiment, the second rotation axis BB of the second revolute pair may be parallel to the third rotation axis CC of the third revolute pair. In one embodiment, the second rotation axis BB may intersect with the third rotation axis CC, i.e. they may not be parallel to each other.

In one embodiment, the first rotation axis AA of the first revolute pair may intersect with the third rotation axis CC of the third revolute pair. In this case, the first rotation axis AA may or may not be perpendicular to the third rotation axis CC.

In one embodiment, the first rotation axis AA of the first rotation revolute pair may be parallel to the fourth rotation axis DD of the fourth revolute pair. In one embodiment, the first rotation axis AA may intersect with the fourth rotation axis DD, i.e. they may not be parallel to each other.

In some embodiments, the connection between the second end of the rotation arm 37 and the second component may be achieved by many suitable ways. It may be a fixed connection or a rotatable connection. The second end of the rotation arm 37 may be directly fixedly or rotatably connected to the second component. Alternatively, intermediate components may also exist.

For example, in one embodiment, the floating mechanism 30 may further include a second connection seat 39. The second connection seat 39 may be connected to the second end of the rotation arm 37 through a fifth revolute pair with a fifth rotation axis EE, and be able to rotate with respect to the rotation arm 37 by the firth revolute pair around the fifth rotation axis EE.

In one embodiment, the second connection seat 39 may be a component which is separate from the second component, and be connected to the second component through a connection device. Alternatively, the second connection seat 39 may be integrated with the second component, i.e. may be a part of the second component.

In one embodiment, the fifth rotation axis EE of the fifth revolute pair may be parallel to the fourth rotation axis DD of the fourth revolute pair. In one embodiment, the fifth rotation axis EE may intersect with the fourth rotation axis DD, i.e. they may not be parallel to each other.

In the embodiment, the first revolute pair, the second revolute pair, the third revolute pair, the fourth revolute pair and the fifth revolute pair may be any suitable revolute pair mechanism, such as revolute pair formed by a rotation pin and a pin hole or by a rotation seat and a rotation shaft, etc. Some examples of the specific structure of the revolute pair will be described in detail below with reference to the drawings. However, it should be understood that the revolute pair will not be limited to the examples to be described in detail below.

In some embodiments, the lifting arm 33 and the rotation arm 37 may be any suitable support arm or connection arm. For example, they may be components formed by a single rod, or formed by multiple parts (such as some embodiments shown in FIG. 4 to FIG. 6). The lifting arm 33 and the rotation arm 37 may be any suitable shapes. For example, they may be straight, curved or other shapes.

In some embodiments above, the lifting arm 33 may be rotatably connected to the first connection seat 31 through the second revolute pair, while the first connection seat 31, itself, may be rotatably connected to the first component through the first revolute pair. Furthermore, since the rotation axes of the first revolute pair and the second revolute pair intersect with each other (i.e., they may not be parallel or coincident with each other), the rotation direction of the first revolute pair may be different from the rotation direction of the second revolute pair. Therefore, the lifting arm 33 may have rotational freedom in two directions (i.e., the rotation directions of the first and the second revolute pairs) with respect to the first component. The rotation arm 37 may be rotatably connected to the connection bracket 349 through the fourth revolute pair, while the connection bracket 349, itself, may be rotatably connected to the lifting arm 33 through the third revolute pair. Furthermore, since the rotation axes of the third revolute pair and the fourth revolute pair intersect with each other (i.e., they may not be parallel or coincident with each other), the rotation direction of the third revolute pair may be different from the rotation direction of the fourth revolute pair. Therefore, the rotation arm 37 may also have rotational freedom in two directions (i.e. the rotation directions of the third and the fourth revolute pairs) with respect to the lifting arm 33. This way, great freedom of movement may exist between the second component connected to the rotation arm 37 and the first component connected to the first connection seat 31, and the movement in many directions or according to many degrees of freedom between the first component and the second component may be achieved simultaneously. For example, in one embodiment, the forward-and-backward translation, left-and-right translation, left-and-right rotation and up-and-down movement of the second component with respect to the first component may be achieved simultaneously. The resultant effect of these movements in many directions or according to many degrees of freedom achieved simultaneously may enable the second component to freely move, with respect to the first component, along any path, to any position within a certain distance from the first component.

In addition, in some embodiments above, in the case that the first rotation axis AA is perpendicular to the second rotation axis BB and/or the second rotation axis BB is parallel to the third rotation axis CC and/or the third rotation axis CC is perpendicular to the fourth rotation axis DD and/or the fourth rotation axis DD is parallel to the fifth rotation axis EE, the movements between two or more of the rotation arm 37 (and the second component connected thereto), the lifting arm 33 and the first connection seat 31 (and the first component connected thereto) will be achieved in directions perpendicular to each other, thereby facilitating the operation of the user.

As mentioned above, in some embodiments, the first component and the second component connected by the floating mechanism 30 may respectively be the frame 11, the control panel or the display 90, or any other suitable component which needs to be connected using the floating mechanism. In one embodiment, the first component and/or the second component may also be other connection arm, support arm or connection rod or other intermediate connection element, and will not be limited to the target component which is desired to be connected.

In some embodiments shown in the drawings, the first connection seat 31 is connected to the frame 11 and the rotation arm 37 is connected to the control panel 50, i.e. the first component is the frame 11 and the second component is the control panel 50. In other embodiments, it may also be possible that the first connection seat 31 is connected to the control panel 50 and the rotation arm is connected to the frame 11, i.e. the first component is the control panel 50 and the second component is the frame 11. In other words, in some embodiments, the first component and the second component will not be limited to certain components.

In one embodiment, one or at least two (for example, two or more) floating mechanisms as described above may be arranged between the first component and the second component. For example, in one embodiment, two floating mechanisms as described above may be arranged between the first component and the second component (for example, as shown in the drawings). Not only can the stability and balance of the connection and supporting between the first component and the second component be ensured, but also the possibility of mutual interference between the movements of the floating mechanism can be reduced. In the case that multiple floating mechanisms as described above are arranged between the first component and the second component, the first connection seats of the floating mechanisms may be separate from each other, or may be shared or partially shared by the floating mechanisms.

In one embodiment, the floating mechanism 30 may be connected between the control panel 50 and the frame 11 so as to enable the control panel 50 to, with respect to the frame 11, not only lift in a vertical plane, but also rotate and translate in a translation plane intersecting with the vertical plane, i.e., to achieve the spatial full floating movements. The control panel 50 may be provided with buttons, knobs or the like such that the user can manipulate the ultrasonic diagnosis apparatus 100 by the control panel 50. One end of the support arm 70 may be connected to the control panel 50, and the display 90 may be connected to the other end of the support arm 70 away from the control panel 50. Results of information processing may be displayed on the display.

Figure 2:
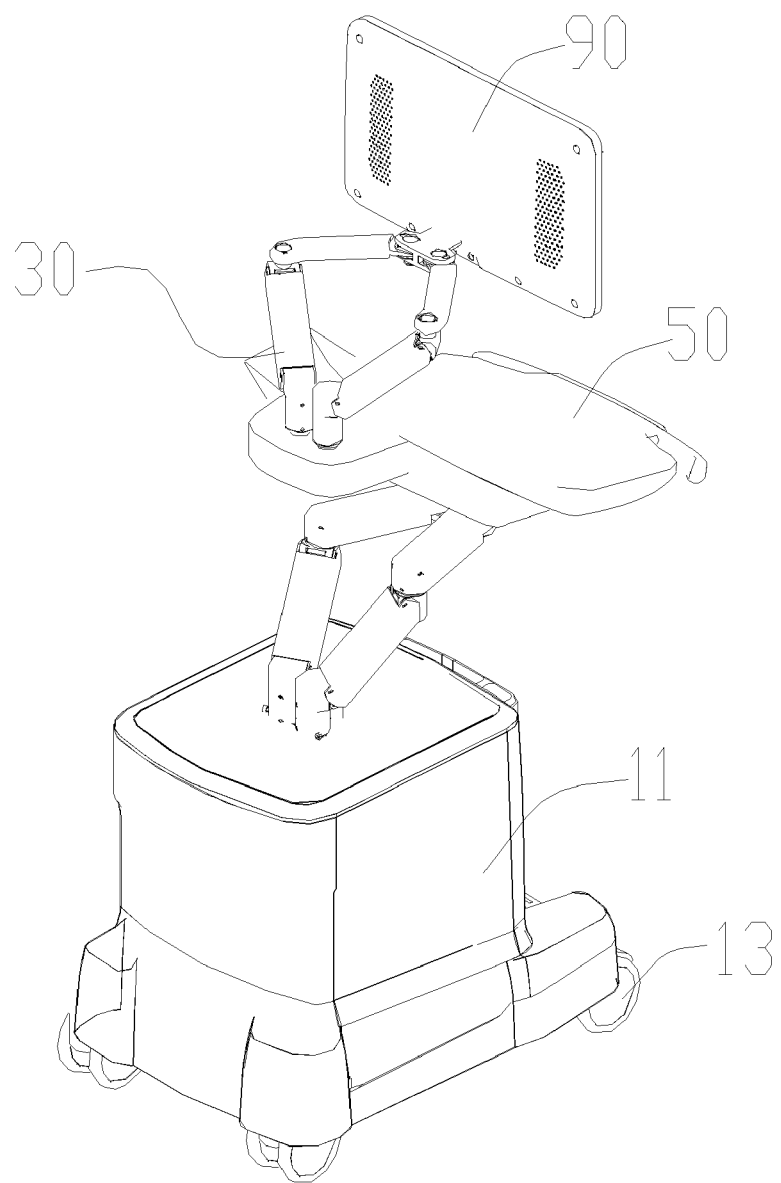
FIG. 2 schematically shows an ultrasonic diagnostic apparatus having a floating mechanism of one embodiment.

In one embodiment, the floating mechanism 30 may be arranged at other positions of the ultrasonic diagnosis apparatus 100, but not limited to the control panel 50. For example, the floating mechanism 30 may be used to achieve the floating movements of the display 90 or other components of which the floating movements are desired. As shown in FIG. 2, the floating mechanism 30 may replace the support arm 70 above to be connected between the control panel 50 and the display 90 to achieve the floating movements of the display 90. Alternatively, the floating mechanism 30 may be arranged between the display and the frame 11 of the main body 10. Specifically, the floating mechanism 30 may include the lifting arm 33, the rotation arm 37 and the connection bracket 349. One end of the lifting arm 33 may be rotatably connected with the connection bracket 349 through a revolute pair, while the connection bracket 349 may be rotatably connected with the rotation arm 37 through a revolute pair. The lifting arm 33 may be able to, taking the end thereof opposite to the rotation arm 37 as a fulcrum, bring the rotation arm 37 to rotate and lift respectively in two planes which intersect with each other, while the rotation arm 37 may be able to rotate in a translation plane intersecting with the lifting arm 33 taking the connection points between the rotation arm 37 and the connection bracket 349 (for example, the revolute pair connecting the rotation arm 37 and the connection bracket 349) as the rotation axis. Taking the end of the lifting arm 33 opposite to the rotation arm 37 as a fulcrum, the lifting arm 33 may have rotational freedoms in two directions in the two planes intersecting with each other.

The floating mechanism 30 may include a support seat 31. The support seat 31 may be mounted on a base on which the floating mechanism 30 is desired to be arranged. In one embodiment, the base may be the frame 11 of the ultrasonic diagnosis apparatus 100. In other embodiments, the base may also be a platform or other support or connection mechanism on which the floating mechanism 30 is desired to be arranged. The support seat 31 may rotate around the axis of itself. The lifting arm 33 may be connected between the support seat 31 and the rotation arm 37. The end of the lifting arm 33 opposite to the rotation arm 37 may be rotatably connected to the support seat 31 through the revolute pair, and may bring the rotation arm 37 to rotate and lift in the two planes intersecting with each other taking the connection points thereof with the support seat 31 as the rotation axis. The rotation arm 37 may be rotatably connected to the connection bracket 349 through the revolute pair, while the connection bracket 349 may be rotatably connected to the other end of the lifting arm 33 opposite to the support seat 31 through the revolute pair. The rotation arm 37 may be able to rotate in a translation plane perpendicular to the axis of the support seat 31 with respect to the lifting arm. In one embodiment, the rotation arm 37 may also be able to rotate in a translation plane which is properly tilted with respect to and not perfectly perpendicular to the axis of the support seat 31.

In one embodiment, one end of the lifting arm 33 may be rotatably connected to the support seat 31 through the revolute pair, and may rotate in the plane in which the axis of the support seat 31 is located taking the connection points of the lifting arm 33 with the support seat 31 (e.g. the revolute pair connecting the lifting arm 33 and the support seat 31) as the rotation axis so as to bring the rotation arm 37 to lift with respect to the support seat 31. The rotation arm 37 may be rotatably connected to the connection bracket 349 through the revolute pair, while the connection bracket 349 may be rotatably connected to the other end of the lifting arm 33 away from the support seat 31 through the revolute pair. The rotation arm 37 may be able to, with respect to the lifting arm 33, rotate in the translation plane perpendicular to the axis of the support seat 31. Since the support seat 31 can rotate around the axis of itself, the support seat 31 may bring the lifting arm 33 and thereby bring the rotation arm 37 to rotate in the translation plane taking the support seat 31 as the fulcrum.

The floating mechanism 30 may include a fixation seat 39 (as shown in FIG. 3). The fixation seat 39 may be rotatably connected to the end of the lifting arm 33 away from the rotation arm 37 through the revolute pair. The rotation axis of the rotatable connection between the fixation seat 39 and the rotation arm 37 (e.g. the fifth rotation axis EE mentioned above) may be parallel to the rotation axis of the support seat 31 (e.g. the first rotation axis AA mentioned above).

Referring to FIG. 3, in one embodiment, two support seats 31 may be arranged on the top of the frame 11 with a distance therebetween. Two lifting arms 33 and two rotation arms 37 may also be arranged, where each lifting arm 33 may be rotatably connected to each rotation arm 37 in a certain angle to form one connection assembly, thereby forming two connection assemblies. The two lifting arms 33 of the two connection assemblies may be rotatably connected to the two support seats 31, respectively. The ends of the two rotation arms 37 away from the corresponding lifting arms 33 may be rotatably connected at two sides of the fixation seat 39. The control panel 50 (or the display 90 or other component desired to be supported by the floating mechanism) may be fixedly mounted on the fixation seat 39 and be able to, with respect to the frame 11, lift in the vertical plane in which the axis of the support seat 31 is located, and translate in forward, backward, left or right directions and rotate in the translation plane along with the two connection assemblies.

The two support seats 31, and the two connection assemblies, may be substantially same to each other in the structure. For the sake of simplicity, the cooperation of only one connection assembly with corresponding support seat 31 is referred below to describe the structure and principles of the floating mechanism 30.

Figure 4:
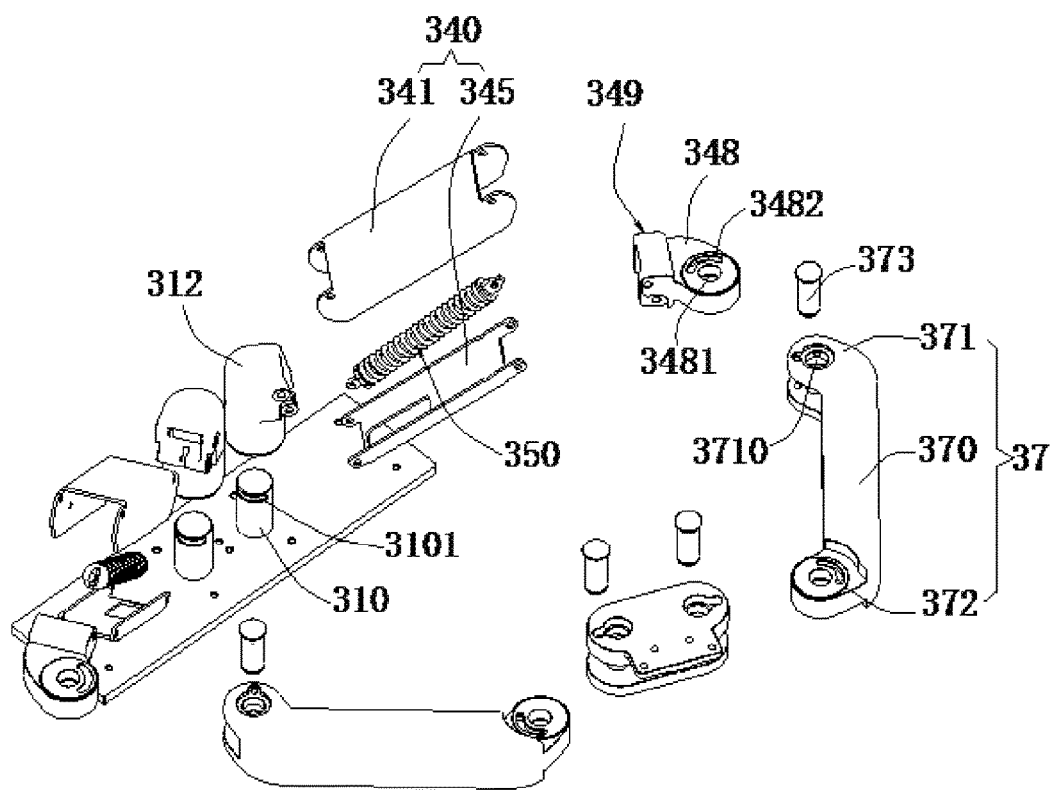
FIG. 4 is an exploded view of the floating mechanism of FIG. 1.
Figure 5:
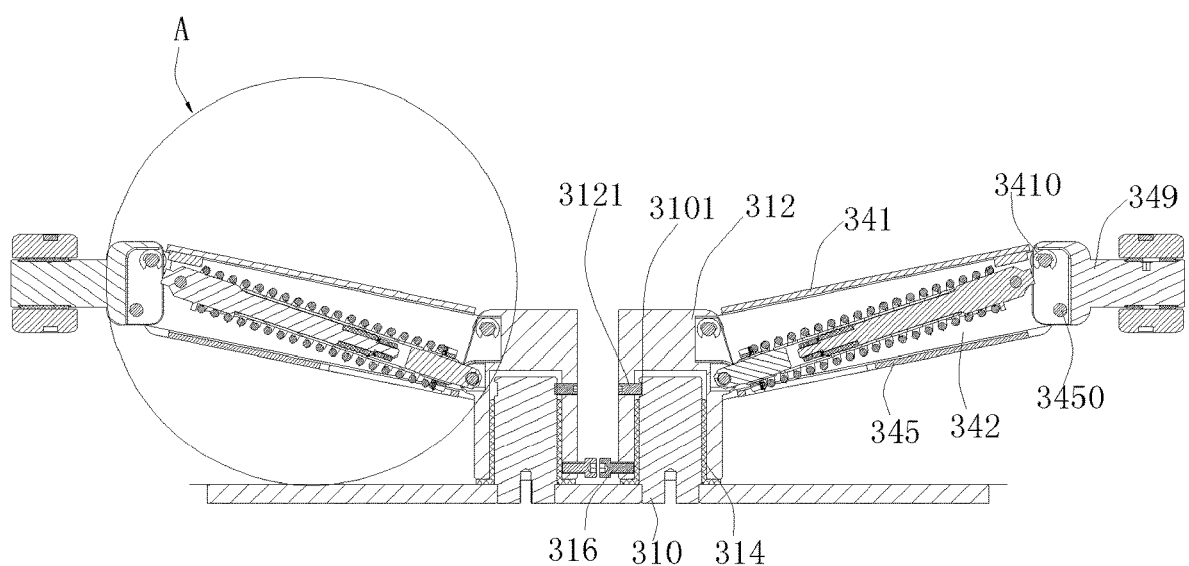
FIG. 5 is a partial sectional view of the floating mechanism of FIG. 4.

Referring to FIG. 4 and FIG. 5, in one embodiment, the support seat 31 may include a column 310 and a rotation element 312. The column 310 may be substantially cylindrical, and fixedly mounted on the frame 11. A limit slot 3101 may be arranged in an outer surface of the column 301 in the circumferential direction. The rotation element 312 may be substantially a hollow cylinder with an open end, and may be rotatably sleeved outside of the column 310 through the open end. This way, the column 310 and the rotation element 312 may form an example of the first revolute pair described above. The inner surface of the rotation element 312 facing the column 310 may be provided with a limit pin 3121. One end of the limit pin 3121 may be inserted into the limit slot 3101 so as to limit the rotation angle of the rotation element 312 with respect to the column 310.

In one embodiment, it may also be possible that only one support seat 31 is arranged at the tope of the frame 11 and the two lifting arms 33 are rotatably connected to the support seat 31 at two sides thereof opposite to each other. The rotation structure of the support seat 31 may be designed according to needs, as long as it can, under an external force, bring the lifting arm 33 and rotation arm 37 of the corresponding connection assembly to rotate in the translation plane with respect to the frame 11. For example, the column 310 may be rotatably mounted on the frame 11, and the rotation element 312 may be sleeved on the column 310 so as to rotate along with the column 310 with respect to the frame 11. Alternatively, the column 310 may be integrated with the rotation element 312 which may be rotatably mounted on the frame 11.

The support seat 31 may further include a bush 314 arranged between the column 310 and the rotation element 312. The bush 314 may be used to reduce the wear of the column 310 and the rotation element 312. The support seat 31 may further include a damping pin 316. The damping pin 316 may pass through the rotation element 312 and abut against the bush 314 so as to adjust the rotation damping force between the column 310 and the rotation element 312.

The lifting arm 33 may include a lifting bracket 340 and a damping balance compensation device 350. The lifting bracket 340 may be connected between the rotation element 312 of the support seat 31 and the connection bracket 349. The damping balance compensation device 350 may be arranged in the lifting bracket 340, and may be used to compensate the change of the torque acting on the lifting arm 33 resulting from the rotation of the lifting arm 33 so as to maintain a balance of the torques acting on the lifting arm 33, thereby stably supporting the control panel 50 and the display 90.

Specifically, the lifting bracket 340 may include an upper bracket 341 and a lower bracket 345. Two ends of the upper bracket 341 may be rotatably connected to the rotation element 312 and the connection bracket 349 through upper revolute pairs 3410, respectively. Two ends of the lower bracket 345 may be rotatably connected to the rotation element 312 and the connection bracket 349 through lower revolute pairs 3450, respectively. The upper bracket 341 and the lower bracket 345 may be parallel to each other, and form a receiving space 342. Two upper revolute pairs 3410 and two lower revolute pairs 3450 may form a parallelogram where the four revolute pairs are located at the four vertices of the parallelogram, respectively. In this embodiment, the two revolute pairs connected with the connection bracket 349 may collectively be an example of the third revolute pair mentioned above, and the two revolute pairs connected with the rotation element 312 may collectively be an example of the second revolute pair mentioned above.

Figure 6:
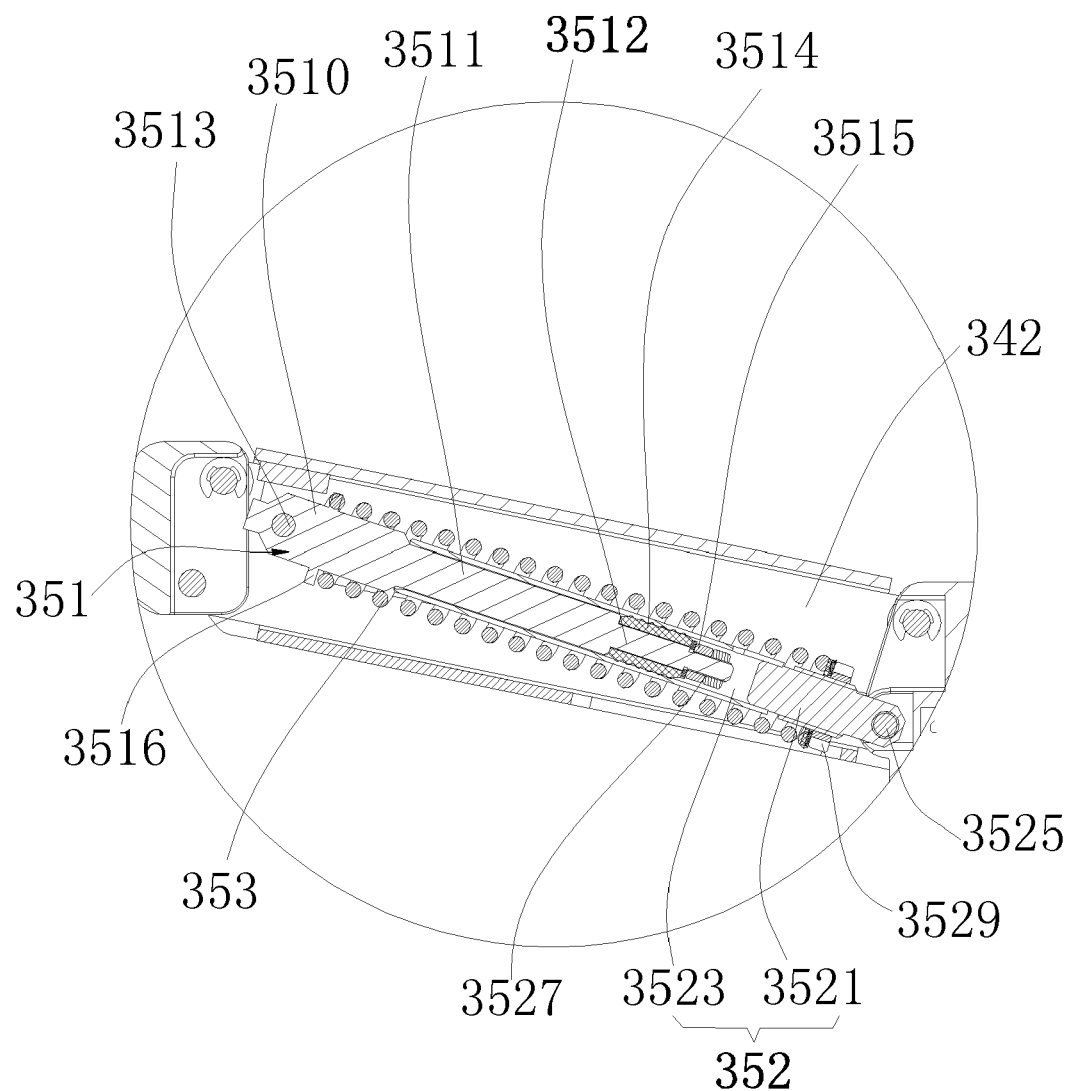
FIG. 6 is an enlarged view of A in the floating mechanism of FIG. 5.

Referring to FIG. 6, the damping balance compensation device 350 may be received in the receiving space 342, and may include a guide rod 351, a guide cylinder 352 and a spring 353. The guide cylinder 352 may include a first connection portion 3521 and an open portion 3523. The first connection portion 3521 may be connected with the rotation element 312 through a connection revolute pair 3525. The open portion 3523 may be depressed inwardly to form a receiving cavity 3527.

The guide rod 351 may include a second connection portion 3510, a first extension portion 3511 and a second extension portion 3512. The second connection portion 3510 may be rotatably connected with the upper bracket 341 of the lifting bracket 340 through a guide rod revolute pair 3513, and an end of the second connection portion 3510 away from the connection bracket 349 may protrude to form the first extension portion 3511. An end of the first extension portion 3511 away from the second connection portion 3510 may protrude to form the second extension portion 3512. The sizes of the second connection portion 3510, the first extension portion 3511 and the second extension portion 3512 may be decreased gradually, such that the guide rod 351 may be a stepped-shape with three steps.

The second extension portion 3512 may be inserted into the receiving cavity 3527 of the guide cylinder 352 through the open portion 3523, and may be moved in the receiving cavity 3527 along an axial direction with respect to the guide cylinder. A friction pad 3514 may be sleeved on the second extension portion 3512 and abutted against an inner surface of the receiving cavity 3527. One end of the friction pad 3514 may be abutted against the connection portion between the second extension portion 3512 and the first extension portion 3511, while the other end may be retained at one end of the second extension portion 3512 away from the first extension portion 3511 by a retaining nut 3511 so as to prevent the friction pad 3514 from falling.

The spring 353 may be sleeved outside the guide rod 351 and the guide cylinder 352, and the guide rod 351 and the guide cylinder 352 may pass through the middle of the spring in the axial direction. Specifically, a flange 3516 may be arranged at the second connection portion 3510 of the guide rod 351, and a spring adjustment nut 3529 may be connected to the outer surface of the first connection portion 3521 of the guide cylinder 352 through screw threads. The spring 353 may be abutted against the flange 3516 in one end and abutted against the spring adjustment nut 3529 in the other end. In this case, the spring 353 may apply a certain trust force on the guide rod 351. The operator may adjust the magnitude of the thrust force applied on the guide rod 351 by the spring 353 by adjusting the distance between the spring adjustment nut 3529 and the flange 3516.

Figure 7A:
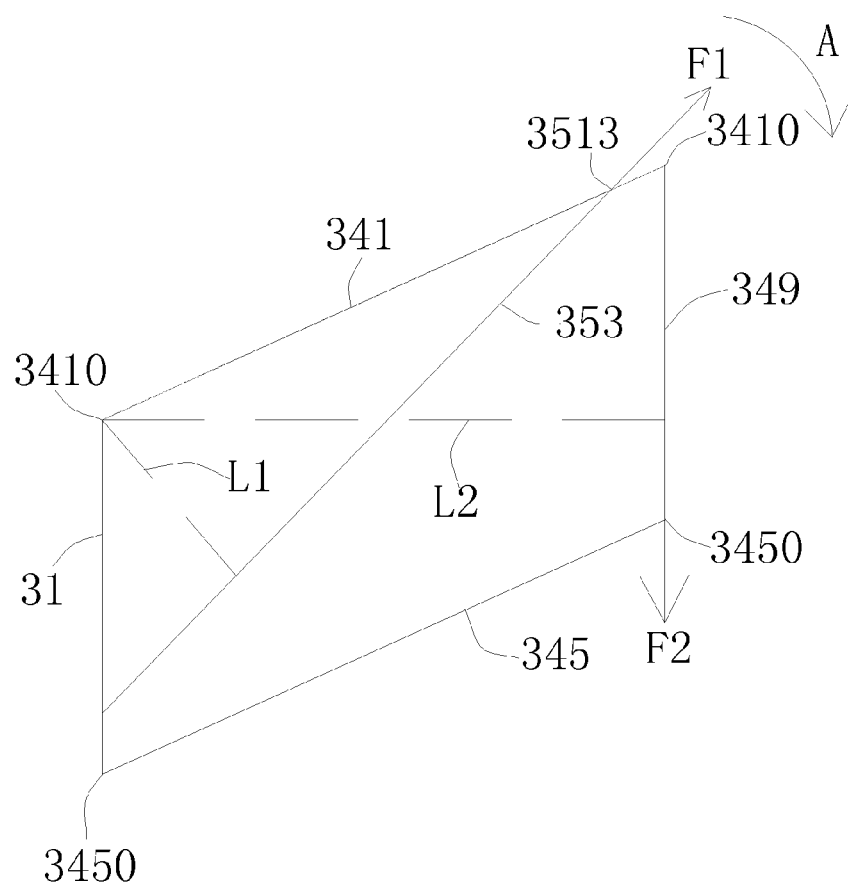
FIG. 7A and FIG. 7B are schematic force analytical graphs of the upper bracket in the floating mechanism of FIG. 5.

A schematic force analytical graph is shown in FIG. 7A, in which 341 represents the upper bracket, 31 represents the support seat, 345 represents the lower bracket, 3410, 3450 and 3513 respectively represent the revolute pairs in the upper bracket 341, the lower bracket 345 and the guide rod 351, 349 represents the connection bracket, and 353 represents the spring. F1 represents the force acted on the upper bracket 341 by the spring 353, with an arm of force L1 and a torque F1×L1. F2 represents the force acted on the upper bracket 341 by components acting on the upper bracket 341 (e.g. the gravities of the control panel 50, the support arm 70 and the display 90 supported by the lifting bracket 340), with an arm of force L2 and a torque F2×L2. The torque of F1 and the torque of F2 are opposite in direction. Therefore, when the arms of force L1 and L2 and the magnitudes of F1 and F2 are properly adjusted such that the magnitude of F1×L1 is equal to the magnitude of F2×L2, the upper bracket 341 will balance, and the components acting on the upper bracket 341 will be supported in balance.

Figure 7B:
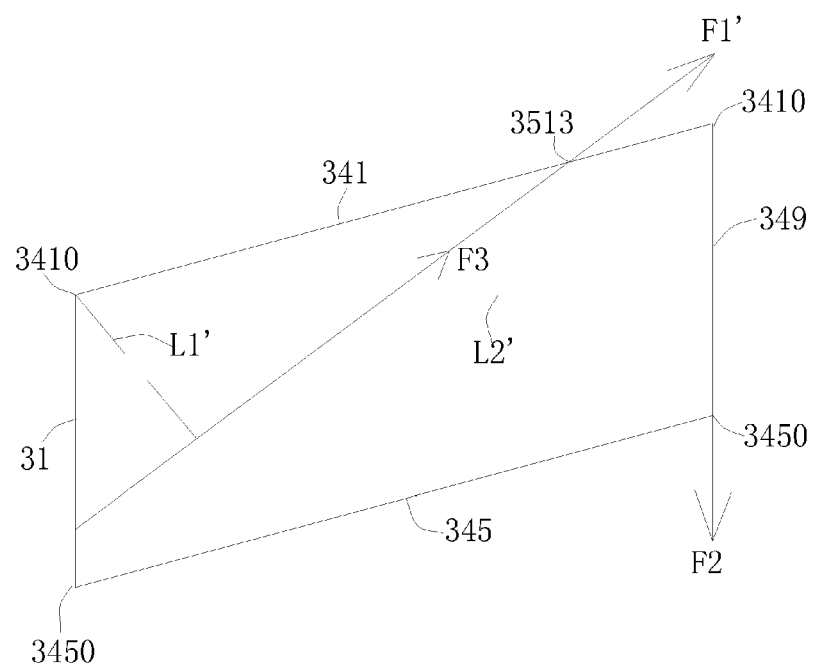

During the work of the ultrasonic diagnosis apparatus 100, the floating mechanism 30 may need to be rotated around the support seat 31 such that the control panel 50 can be rotated upward or downward by a certain angle. As shown in FIG. 7A, the upper bracket 341 may be rotated by an angle in a direction indicated by the arrow A. When the upper bracket 341 is rotated to a new position, the length of the spring 353 is changed. In other words, the compression of the spring 353 is changed. Therefore, at the new position, the force F1 acted on the upper bracket 341 is changed. Because the upper bracket 341 is rotated by an angle, the arms of force of F1 and F2 are changed. As shown in FIG. 7B, F1' represents the force acted on the upper bracket 341 by the spring 353 at the new position, L1' represents the arm of force of F1' at the new position, and L2' represents the arm of force of F2 at the new position. In this case, the magnitude of F1'×L1' may not be equal to that of F2×L2'. If there is no additional compensation torque, the torques acting on the upper bracket 341 may not be balanced, and the upper bracket 341 may be unable to steadily support the control panel 50 and the display 90 at desired position.

In some embodiments of the present disclosure, such change of the torque can be compensated. As shown in FIG. 6, in one embodiment, the friction pad 3514 may be sleeved on the second extension portion 3512 of the guide rod 351. The friction pad 3514 may be abutted against the inner surface of the receiving cavity 3527 of the guide cylinder. As shown in FIG. 7B, when the torque of F2 is larger than that of F1' at the new position, the upper bracket 341 has a tendency to rotate downward, which leads to that the guide rod 351 has a tendency to move toward the guide cylinder 352 in the axial direction, i.e. the guide rod 351 has a tendency to move into the receiving cavity 3527 of the guide cylinder 352. At this time, since the friction pad 3514 sleeved on the second extension portion 3512 of the guide rod 351 is abutted against the inner surface of the receiving cavity 3527 of the guide cylinder 352, static friction force is generated between the friction pad 3514 and the inner surface of the receiving cavity 3527. It can be known based on characteristics of static friction force that the static friction force F3 (as shown in FIG. 7B) acting on the guide rod 351 has a same direction with F1'. Since the guide rod 351 is connected with the upper bracket 341, the friction force F3 will act on the upper bracket 341, and the torque thereof will have a direction which is the same with F1' and opposite to F2. Therefore, the torque of F3 can compensate the difference between the torque of F1' and the torque of F2 so as to balance the torques acting on the upper bracket 341 and keep the total torque acting on the upper bracket 341 being zero. Similarly, when the upper bracket 341 is rotated in an opposite direction such that the torque of F1 cannot be balanced with the torque of F2, the analysis may be similar to that described above and will not be described in detail.

In some embodiments, the force of the spring 353 may be used to balance the torques acting on the upper bracket 341, and the static friction force between the friction pad 3514 arranged on the guide rod 351 and the inner surface of the guide cylinder 352 may be used to further compensate and balance the torques acting on the upper bracket 341, such that the upper bracket 341 can be kept balance in any position. Furthermore, in that case that the force of the spring is attenuated, such attenuation of the force of the spring can be compensated by the static friction force so as to keep the balance of the upper bracket 341, thereby providing steady support for the control panel 50 and the display 90. It can be understood that in other embodiments the damping compensation device 350 may also be implemented by other ways, which will not be limited. For example, a gas spring, an extension spring or a torsion spring may be used.

Figure 8:
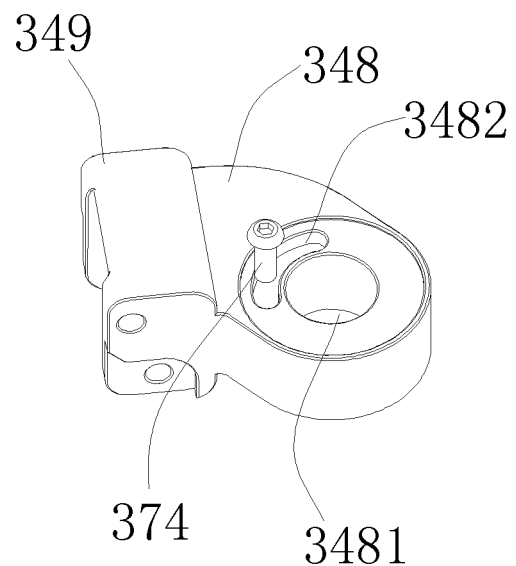
FIG. 8 schematically shows the connection bracket of the floating mechanism of FIG. 4.

Referring to FIG. 8, the connection bracket 349 may be provided with a first protrusion portion 348 protruding from a side of the connection bracket 349 away from the support seat 31. The first protrusion portion 348 may be formed by arcuately extending an edge of the connection bracket 349 opposite to the guide rod 351, and be provided with a first shaft hole 3481 which may be used to be rotatably connected with the corresponding rotation arm 37. A curved first groove 3482 may be arranged in the first protrusion portion 348. The first groove 3482 may be around the first shaft hole 3481 along a circumference direction of the first shaft hole 3481 and used to limit the rotation angle of the rotation arm 37 with respect to the lifting arm 33. In one embodiment, the two first protrusion portions 348 of the two connection brackets 349 may be formed by bending inwardly towards each other such that the shape formed by the lines connecting the two support seats 31, the two connection assemblies and the fixation seat 39 is a hexagon. In other embodiments, the two first protrusion portion 348 may also be formed by bending outwardly away from each other, which will not be limited in the present disclosure.

Referring to FIG. 4, the rotation arm 37 may include an arm portion 370, and a first rotation portion 371 and a second protrusion portion 372 arranged respectively at two ends of the arm portion 370. The first rotation portion 371 may substantially be U-shape with an opening facing the first protrusion portion 348 of the connection bracket 349, and two ends of the first rotation portion 371 may be respectively provided with first rotation shaft holes 3710 corresponding to the first shaft hole 3481 in the first protrusion portion 348. The first protrusion portion 348 may be inserted between the two ends of the first rotation portion 371 and the shaft 373 may pass through the first shaft hole 3481 and the first rotation shaft holes 3710, thereby rotatably connecting the rotation arm 37 and the connection bracket 349. Furthermore, the first rotation portion 371 may be further provided with a first pin 374 (as shown in FIG. 8) which may be inserted into the first groove 3482 so as to limit the rotation angle of the first rotation portion 371 with respect to the first protrusion portion 348. In the present embodiment, the shaft 373 and the first shaft hole 3481 and the first rotation shaft holes 3710 may be an example of the fourth revolute pair.

Figure 9:
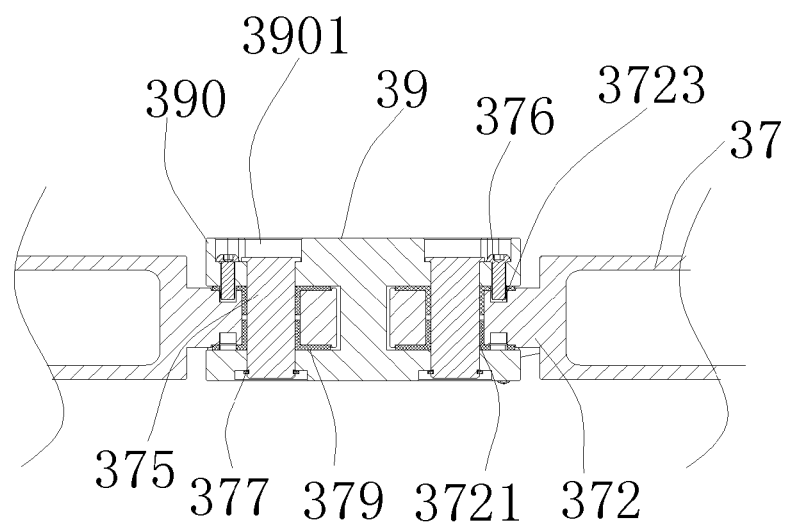
FIG. 9 is a sectional view of the rotation arm and the fixation seat of the floating mechanism of FIG. 4.

Referring to FIG. 9, the shape of the second protrusion portion 372 may be substantially the same with the shape of the first protrusion portion 348. A second shaft hole 3721 and a curved second groove 3723 arranged at outside, and along the circumference direction, of the second shaft hole 3721 may be arranged in the second protrusion portion 372. Second rotation portions 390 cooperating with the two second protrusion portions 372 of the two rotation arms 37 may be arranged at two ends of the fixation seat 39. The shape of the second rotation portion 390 may be substantially the same to the shape of the first rotation portion 371, and may be provided with second rotation shaft holes 3901 corresponding to the second shaft hole 3721 of the second protrusion portion 372. The second protrusion portion 372 may be inserted between the two ends of the second rotation portion 390, and the shaft 375 may pass through the second shaft hole 3721 and the second rotation shaft holes 3901 and be fixed on the fixation seat 39 by a retaining ring 377, thereby rotatably connecting the rotation arm 37 and the fixation seat 39. Furthermore, the second rotation portion 390 may be further provided with a second pin 376 which may be inserted into the second groove 3723 so as to limit the rotation angle of the second rotation portion 390 with respect to the second protrusion portion 372.

The rotation arm 37 may further include a bush 379 which may be arranged between the shaft 375 and the second protrusion portion 372 corresponding thereto so as to reduce the wear of the shaft 375 and the second protrusion portion 372.

Figure 10A:
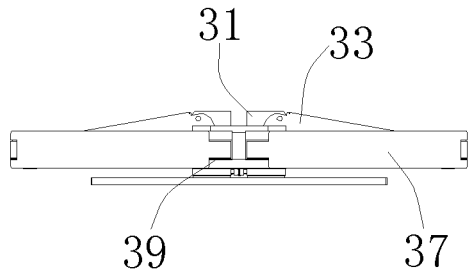
FIG. 10A-10L schematically show the movement of the floating mechanism of FIG. 3.
Figure 10B:
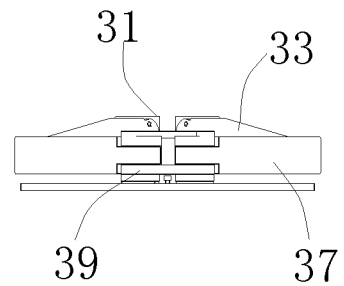
Figure 10C:
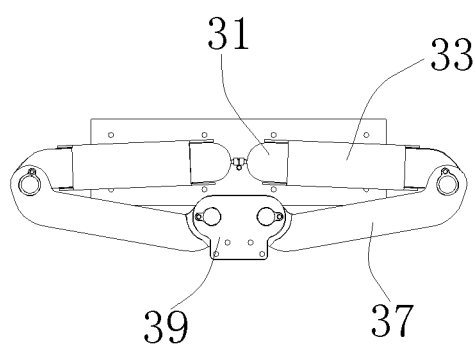
Figure 10D:
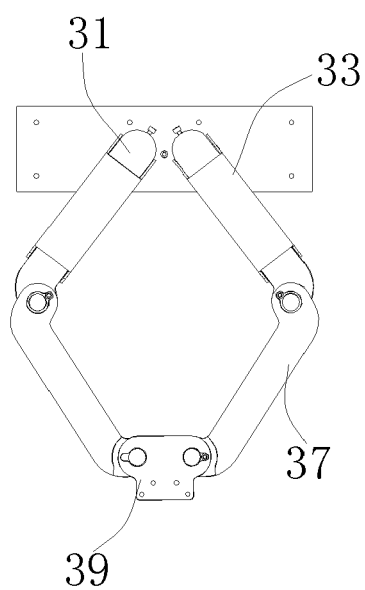
Figure 10E:
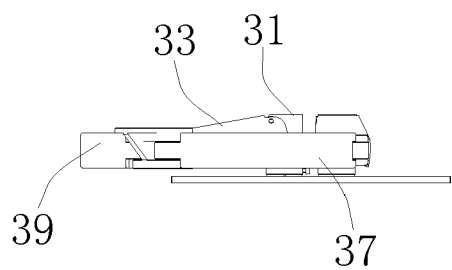
Figure 10F:
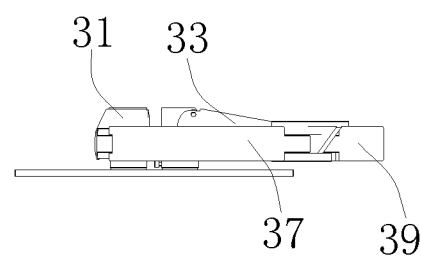
Figure 10G:
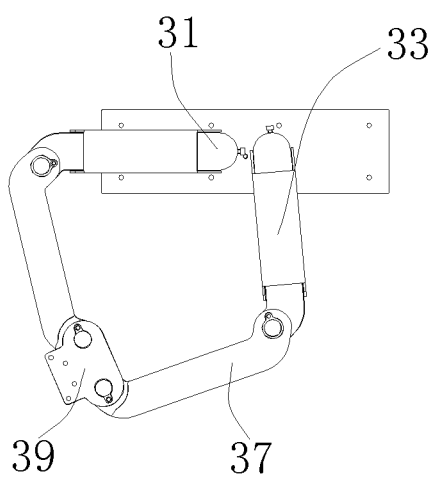
Figure 10H:
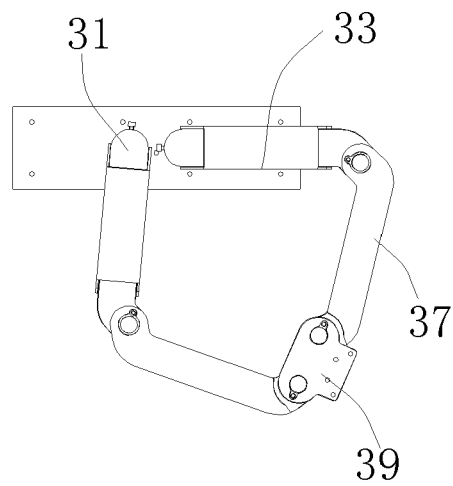
Figure 10I:
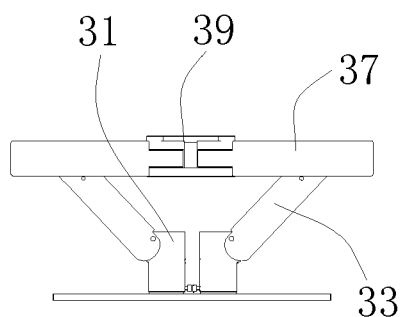
Figure 10J:
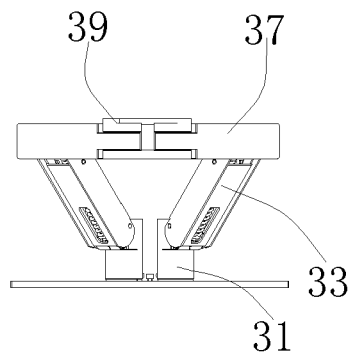
Figure 10K:
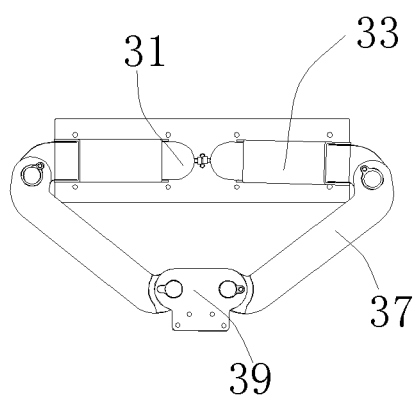
Figure 10L:
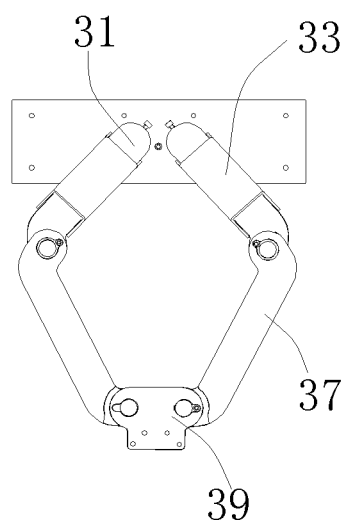

Referring to FIG. 10A through FIG. 10O, during the manipulation, the operator may control the movement of the control panel 50 by manipulating the floating mechanism 30. For example, when the control panel 50 needs to be lifted, the lifting arm 33 may be rotated through its upper revolute pair 3410 and lower revolute pair 3450 with respect to the rotation element 312 of the support seat 31 in a vertical plane so as to rise or fall, thereby bringing the rotation arm 37 and the control panel 50 fixed on the fixation seat 39 to be lifted with respect to the frame 11. When the control panel 50 needs to be rotated to the left or right, the lifting arm 33 may be rotated around the column 310 to the left or right together with the rotation element 312, thereby bringing the control panel 50 fixed on the rotation arm 37 to move. When the control panel 50 needs to be translated forward or backward, the rotation arm 37 may be rotated around the shaft 373 with respect to the connection bracket 349, thereby bringing the control panel 50 to move. In actual operation, the movements mentioned above may be achieved one or more simultaneously, which will not be limited.

Figure 11A:
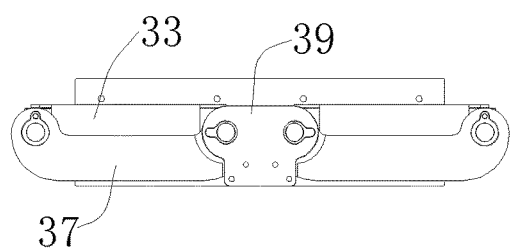
FIG. 11A-11C schematically show the floating mechanism of one embodiment.
Figure 11B:
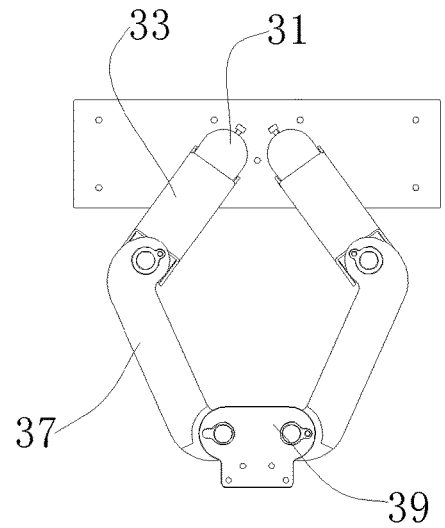
Figure 11C:
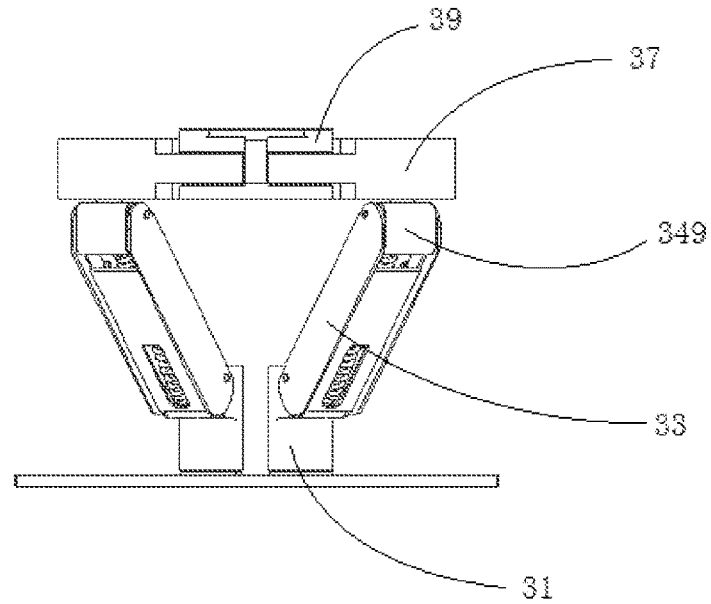

In some embodiments of FIG. 3-6 and FIG. 9, the connection bracket 349 is arranged horizontally, i.e. the direction from the third revolute pair connected to the connection bracket 349 to the fourth revolute pair connected to the connection bracket 349 (or vice versa) is in the horizontal direction. However, the present disclosure will not be limited thereto. In other embodiment, the connection bracket 349 may also be arranged in a vertical direction or other direction. For example, referring to FIG. 11A through FIG. 11C, in one embodiment, the connection bracket 349 may be arranged in a vertical direction, i.e. the direction from the third revolute pair connected to the connection bracket 349 to the fourth revolute pair connected to the connection bracket 349 (or vice versa) is in a vertical direction. This way, the rotation arm 37 may be at least partially vertically rotatably connected to the top portion of the lifting arm 33, thereby reducing the space occupied by the floating mechanism 30 in the direction perpendicular to the vertical direction.

Figure 12A:
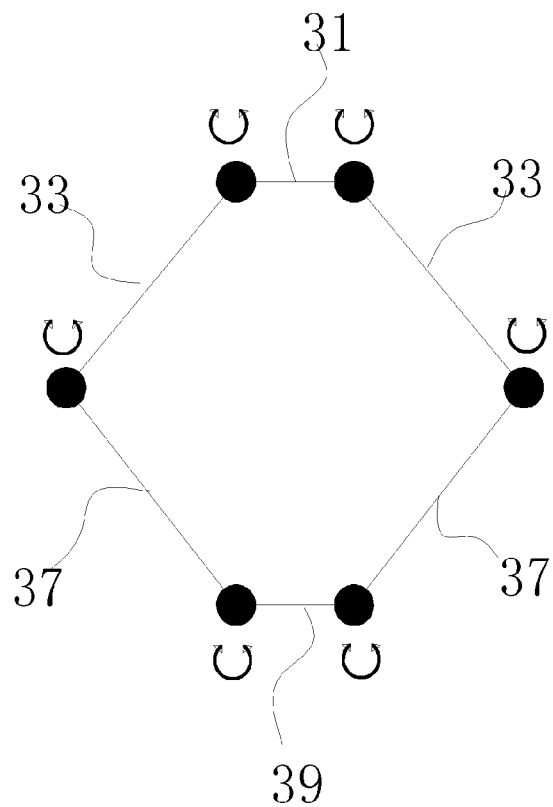
FIG. 12A schematically shows the lines connecting the components of the floating mechanism of FIG. 3.
Figure 12B:
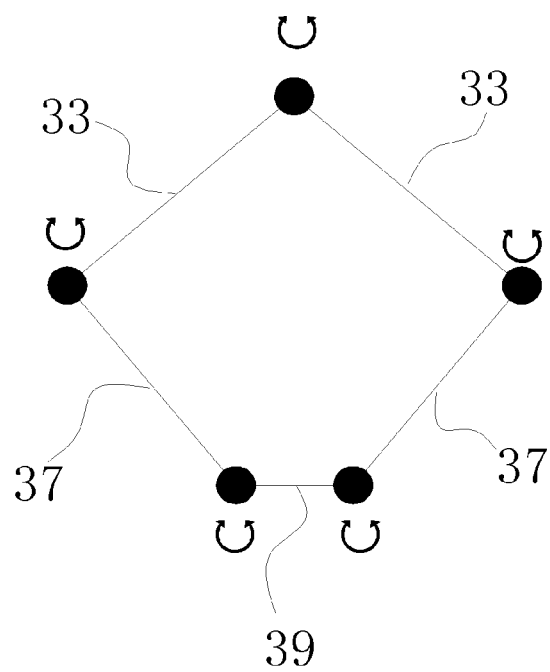
FIG. 12B-12D schematically show variations of the floating mechanism.
Figure 12C:
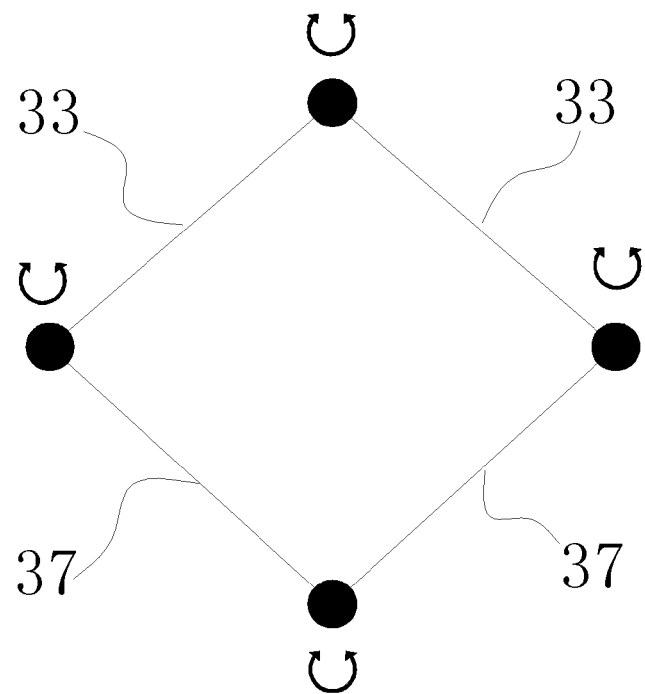
Figure 12D:
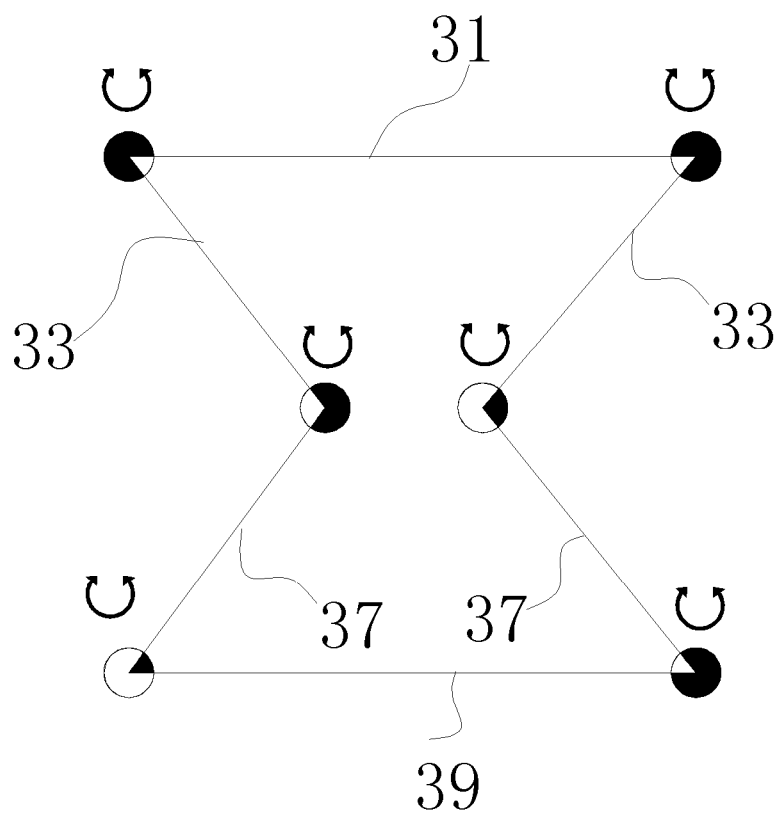

Referring to FIG. 12A through FIG. 12D, in the present disclosure, the connection between the two connection assemblies may be designed as needed. For example, in one embodiment, the lines connecting the two connection assemblies, two support seats 31 and the fixation seat 39 may form a hexagon (as shown in FIG. 12A). In another embodiment, there may be only one support seat 31 and the two lifting arms 33 of the two connection assemblies may be connected to two sides of this support seat 31. In this case, the lines connecting the components of the floating mechanism 30 may form a pentagon (as shown in FIG. 12B). In one embodiment, the fixation seat 39 may further be omitted and the adjacent ends of the two rotation arms 37 may be rotatably connected with each other. In this case, the lines connecting the components of the floating mechanism 30 may form a quadrilateral (as shown in FIG. 12C). In one embodiment, the two first protrusion portions 348 of the connection brackets 349 of the two connection assemblies may be bent away from each other. In this case, the floating mechanism 30 may be a four-bar eversion structure (as shown in FIG. 12D).

In some embodiments, the lifting arm 33 of the floating mechanism 30 may be rotatably connected to the support seat 31 along the axial direction thereof, and be rotatably connected with the rotation arm 37 through the connection bracket 349, such that the lifting arm 33 and the rotation arm 37 may collectively bring the control panel 50 to lift in a plane in which the axis of the support seat 31 is located and to translate forward or backward or to the left or to the right in the translation plane. Furthermore, since the support seat 31 can be rotated around its axis, the control panel 50 may also be rotated with the lifting arm 33 and the rotation arm 37 in the translation plane. The floating mechanism 30 has large operation range, good linkage and small occupied space, and can achieve the lifting in a vertical plane and the translation and rotation in a translation plane.

Several embodiments have been described above. The description is specific and detailed. However, the description above should not be interpreted as limitations to the present disclosure. Many modifications and improvements may be made by a person ordinarily skilled in the art without departing from the concepts of the present disclosure, which all belong to the scope of protection of the present disclosure. Therefore, the protection scope of the present disclosure shall be defined by the claims below.

What is claimed is:

1. A floating mechanism, comprising:
a lifting arm;
a rotation arm;
a connection bracket, wherein an end of the lifting arm is rotatably connected with the connection bracket, the connection bracket is rotatably connected with an end of the rotation arm, the lifting arm brings the rotation arm to rotate and lift respectively in two planes intersecting with each other taking the other end of the lifting arm away from the rotation arm as a fulcrum, and the rotation arm rotates in a translation plane intersecting with the lifting arm around a connection point between the rotation arm and the connection bracket; and
a support seat, wherein an end of the lifting arm away from the rotation arm is rotatably connected to the support seat, and the lifting arm brings the rotation arm to rotate and lift respectively in two planes intersecting with each other taking the support arm as a fulcrum;
wherein the support seat comprises a column and a rotation element rotatably sleeved on the column, an end of the lifting arm is rotatably connected to the rotation element, and the lifting arm is able to bring the rotation arm to rotate around the column together with the rotation element.

2. The floating mechanism of claim 1, wherein the lifting arm has rotation freedoms in two directions respectively in the two planes intersecting with each other taking the other end of the lifting arm away from the rotation arm as a fulcrum.

3. The floating mechanism of claim 1, wherein two lifting arms and two rotation arms are arranged such that one lifting arm and one rotation arm are rotatably connected through the connection bracket in an angle to form one connection assembly, thereby forming two connection assemblies, and two connection ends between the lifting arms and the rotation arms of the two connection assemblies are close to or away from each other.

4. The floating mechanism of claim 1, wherein the support seat is able to rotate around an axis thereof to bring the lifting arm, which brings the rotation arm, to rotate in the translation plane taking the support seat as a fulcrum, the lifting arm is able to bring the rotation arm to lift with respect to the support seat in a plane in which an axis of the support seat is located, and the rotation arm is rotatably connected with the connection bracket and is able to rotate with respect to the lifting arm in the translation plane perpendicular to the axis of the support seat.

5. The floating mechanism of claim 1, wherein one support seat or two support seats separate from each other are arranged, such that two lifting arms and two rotation arms are arranged, and two ends of the two lifting arms are rotatably connected respectively to two sides of the one support seat or to the two support seats.

6. The floating mechanism of claim 1, wherein a limit slot is arranged in an outer surface of the column in a circumferential direction, a limit pin is arranged in an inner surface of the rotation element facing the column, and the limit pin is inserted into the limit slot.

7. The floating mechanism of claim 1, wherein the support seat further comprises a damping pin and a bush arranged between the column and the rotation element, and the damping pin passes through the rotation element and abuts against the bush.

8. A floating mechanism, comprising:
a lifting arm;
a rotation arm;
a connection bracket, wherein an end of the lifting arm is rotatably connected with the connection bracket, the connection bracket is rotatably connected with an end of the rotation arm, the lifting arm brings the rotation arm to rotate and lift respectively in two planes intersecting with each other taking the other end of the lifting arm away from the rotation arm as a fulcrum, and the rotation arm rotates in a translation plane intersecting with the lifting arm around a connection point between the rotation arm and the connection bracket; and
a support seat, wherein an end of the lifting arm away from the rotation arm is rotatably connected to the support seat, and the lifting arm brings the rotation arm to rotate and lift respectively in two planes intersecting with each other taking the support arm as a fulcrum;
wherein the lifting arm comprises a lifting bracket, the lifting bracket comprises an upper bracket and a lower bracket, two ends of the upper bracket are respectively rotatably connected to the rotation element and the connection bracket through upper revolute pairs, two ends of the lower bracket are respectively rotatably connected to the rotation element and the connection bracket through lower revolute pairs, two upper revolute pairs and two lower revolute pairs form a parallelogram where four revolute pairs are respectively located at four vertices of the parallelogram.

9. The floating mechanism of claim 8, wherein a first protrusion portion is protruded from a side of the connection bracket away from the support seat, and a first shaft hole is arranged in the first protrusion portion which is used to be rotatably connected with corresponding rotation arm.

10. The floating mechanism of claim 9, wherein a curved first groove is arranged at an outside of the first shaft hole along a circumference direction, the rotation arm comprises a first rotation portion which is rotatably connected to the first protrusion portion, and the first rotation portion is provided with a first pin which is inserted into the first groove.

11. A floating mechanism, comprising:
a lifting arm;
a rotation arm;
a connection bracket, wherein an end of the lifting arm is rotatably connected with the connection bracket, the connection bracket is rotatably connected with an end of the rotation arm, the lifting arm brings the rotation arm to rotate and lift respectively in two planes intersecting with each other taking the other end of the lifting arm away from the rotation arm as a fulcrum, and the rotation arm rotates in a translation plane intersecting with the lifting arm around a connection point between the rotation arm and the connection bracket:
a support seat, wherein an end of the lifting arm away from the rotation arm is rotatably connected to the support seat, and the lifting arm brings the rotation arm to rotate and lift respectively in two planes intersecting with each other taking the support arm as a fulcrum; and a fixation seat, wherein the fixation seat is rotatably connected to an end of the rotation arm away from the lifting arm, and a rotation axis around which the fixation seat is rotatably connected to the rotation arm is parallel to a rotation axis of the support seat;
wherein the fixation seat comprises a second rotation portion rotatably connected to the rotation arm, the rotation arm comprises a second protrusion portion which is provided with a second shaft hole used to be rotatably connected with the second rotation portion, a curved second groove is arranged at outside of the second shaft hole and along a circumference direction, and the second rotation portion is provided with a second pin which is inserted into the second groove.

12. The floating mechanism of claim 11, wherein the rotation arm comprises a bush, a shaft and a retaining ring, the second rotation portion is provided with a second rotation shaft hole corresponding to the second shaft hole of the second protrusion portion, the shaft passes through the second shaft hole and the second rotation shaft hole and fixed on the fixation seat by the retaining ring, and the bush is arranged between the shaft and the second protrusion portion.

13. A floating mechanism used to connect a first component and a second component, comprising: a first connection seat which is connected to the first component through a first revolute pair with a first rotation axis and is able to rotate with respect to the first component around the first rotation axis; a lifting arm comprising a first end and a second end opposite to the first end, wherein the first end of the lifting arm is connected to the first connection seat through a second revolute pair with a second rotation axis and is able to rotate with respect to the first connection seat around the second rotation axis, and the second rotation axis is not parallel to the first rotation axis; a connection bracket which is connected to a second end of the lifting arm through a third revolute pair with a third rotation axis and is able to rotate with respect to the lifting arm around the third rotation axis; and a rotation arm comprising a first end and a second end, wherein the first end of the rotation arm is connected to the connection bracket through a fourth revolute pair with a fourth rotation axis and is able to rotate with respect to the connection bracket around the fourth rotation axis, and the fourth rotation axis is not parallel to the third rotation axis;
wherein the second end of the rotation arm is connected to the second component.

14. The floating mechanism of claim 13, wherein the third rotation axis is perpendicular to the fourth rotation axis.

15. The floating mechanism of claim 13, wherein the third rotation axis is parallel to the second rotation axis.

16. The floating mechanism of claim 13, wherein the first rotation axis is perpendicular to at least one of the second rotation axis and the third rotation axis.

17. The floating mechanism of claim 13, wherein the first rotation axis is parallel to the fourth rotation axis.

18. The floating mechanism of claim 13, further comprising a second connection seat, wherein the second connection seat is connected to the second end of the rotation arm through a fifth revolute pair with a fifth rotation axis and is able to rotate with respect to the rotation arm around the fifth rotation axis, and the second connection seat is connected with the second component.

19. The floating mechanism of claim 18, wherein the fourth rotation axis is parallel to the fifth rotation axis.

20. An ultrasonic diagnostic apparatus, comprising a main body, a control panel, a display and at least one floating mechanism, wherein the floating mechanism is connected between the control panel or the display and the main body, or between the control panel and the display, and comprises: a first connection seat which is connected to the first component through a first revolute pair with a first rotation axis and is able to rotate with respect to the first component around the first rotation axis; a lifting arm comprising a first end and a second end opposite to the first end, wherein the first end of the lifting arm is connected to the first connection seat through a second revolute pair with a second rotation axis and is able to rotate with respect to the first connection seat around the second rotation axis, and the second rotation axis is not parallel to the first rotation axis; a connection bracket which is connected to a second end of the lifting arm through a third revolute pair with a third rotation axis and is able to rotate with respect to the lifting arm around the third rotation axis; and a rotation arm comprising a first end and a second end, wherein the first end of the rotation arm is connected to the connection bracket through a fourth revolute pair with a fourth rotation axis and is able to rotate with respect to the connection bracket around the fourth rotation axis, and the fourth rotation axis is not parallel to the third rotation axis; wherein the second end of the rotation arm is connected to the second component.

21. The ultrasonic diagnostic apparatus of claim 20, comprising at least two floating mechanisms, wherein the at least two floating mechanisms are connected between the control panel or the display and the main body, or between the control panel and the display.

22. The ultrasonic diagnostic apparatus of claim 21, wherein two first connection seats of the at least two floating mechanisms are separate from each other.

\* \* \* \* \*